(12) United States Patent
Zhang et al.

(10) Patent No.: US 8,082,019 B2
(45) Date of Patent: Dec. 20, 2011

(54) SYSTEM AND METHOD FOR MAGNETIC RESONANCE BRAIN SCAN PLANNING

(75) Inventors: Li Zhang, Skillman, NJ (US); Carol Novak, Newtown, PA (US); Hong Chen, Plainsboro, NJ (US); Qing Xu, Nashville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 940 days.

(21) Appl. No.: 11/856,104

(22) Filed: Sep. 17, 2007

(65) Prior Publication Data

US 2008/0071163 A1 Mar. 20, 2008

Related U.S. Application Data

(60) Provisional application No. 60/826,251, filed on Sep. 20, 2006.

(51) Int. Cl.
*A61B 5/00* (2006.01)
(52) U.S. Cl. ......... 600/410; 382/128; 382/173; 324/307
(58) Field of Classification Search .................. 382/128, 382/173; 600/410, 425, 407; 324/307
See application file for complete search history.

(56) References Cited

U.S. PATENT DOCUMENTS

| 5,078,141 | A | 1/1992 | Suzuki et al. | |
|---|---|---|---|---|
| 5,652,515 | A | 7/1997 | Kondo | |
| 6,138,302 | A | 10/2000 | Sashin et al. | |
| 7,450,983 | B2 * | 11/2008 | Weiss | 600/410 |
| 2004/0240753 | A1 | 12/2004 | Hu et al. | |
| 2005/0165294 | A1 | 7/2005 | Weiss | |
| 2006/0251310 | A1 | 11/2006 | Hu et al. | |
| 2007/0014457 | A1 * | 1/2007 | Jolly et al. | 382/128 |
| 2007/0276219 | A1 * | 11/2007 | K.N. et al. | 600/410 |
| 2008/0037848 | A1 * | 2/2008 | Xu et al. | 382/131 |
| 2008/0285829 | A1 * | 11/2008 | Wang et al. | 382/131 |
| 2009/0093706 | A1 * | 4/2009 | Zhang et al. | 600/410 |

OTHER PUBLICATIONS

Y. Liu, R.T. Collins, and W.E. Rothfus, "Robust Midsagittal Plane Extraction from Normal and Pathological 3-D Neuroradiology Images," IEEE Transactions on Medical Imaging, vol. 20, No. 3, pp. 175-192, Mar. 2001.*
B. van Ginneken, A.F. Frangi, J.S. Staal, B.M. ter Haar Romeny, and M.A. Viergever, "Active Shape Model Segmentation with Optimal Features," IEEE Transactions on Medical Imaging, vol. 21, No. 8, pp. 924-934, Aug. 2002.*
U.S. Appl. No. 09/782,828, filed Jul. 25, 2007, Xu et al.

* cited by examiner

*Primary Examiner* — Brian Casler
*Assistant Examiner* — Amanda Lauritzen

(57) ABSTRACT

A method and system for automatic MR brain scan planning is disclosed. The method utilizes a set of 2D orthogonal localizer images to determine scanning planes for 3D diagnostic MR scans. A location of the mid-sagittal plane (MSP) is detected in each of a transversal localizer image and a coronal localizer image. A sagittal scanning plane is determined based on the location of the MSP in the transversal and coronal localizer images. A diagnostic sagittal MR scan is then acquired based on the sagittal scanning plane. The corpus callosum CC is segmented in a sagittal MR image slice resulting from the diagnostic sagittal MR scan. A transversal scanning plane can be determined based on a location of the CC in the sagittal MR image slice and the location of the MSP in the coronal localizer image, and a coronal scanning plane can be determined based on the location of the CC in the sagittal MR image slice and the location of the MSP in the transversal localizer image.

19 Claims, 14 Drawing Sheets

— — — — Manually defined scanning planes

▨ Relevant landmarks

▦ Irrelevant landmarks

Example A

Example B

SYSTEM AND METHOD FOR MAGNETIC RESONANCE BRAIN SCAN PLANNING

This application claims the benefit of U.S. Provisional Application No. 60/826,251, filed Sep. 20, 2006, the disclosure of which is herein incorporated by reference.

BACKGROUND OF THE INVENTION

The present invention relates to magnetic resonance brain scanning, and more particularly, to automatic magnetic resonance brain scan planning.

Magnetic Resonance (MR) is a well known technique for imaging internal organs of a patient. MR scanners are typically capable of generating cross-sectional images in any plane of the body, including oblique planes. Accordingly, the MR volume data resulting from MR scans can have many possible orientations. In MR brain scanning, planning is needed in order to determine the orientation and position of the scanning volumes. In a typical MR brain scan process, an MR operator first acquires scout/localizer images by a short time sequence. The operator then manually plans a 3D diagnostic, which typically take a longer time, scan from the localizer images. The operator can plan other diagnostic scans from available images using anatomic landmarks. However, different hospitals, departments, and operators many use different anatomic landmarks to plan the scanning. Even when the same anatomic landmarks are used, the scanning can be executed inconsistently, due to inter- or intra-operator variation. This can cause variations in the position and orientation of various MR brain scans, which can lead to problems with diagnosis when using MR brain images generated from MR brain scans. Thus, automated and consistent MR scan planning is desirable in clinical MR scanning applications.

Various methods have been proposed for automating the MR brain scanning process. However, such methods require a 3D scout scan for registration. This type of 3D scout imaging is only used for the planning algorithm, not for diagnostic purposes. During the planning of the MR brain scan, a patient must lie absolutely still in a confined space of the MR scanning machine. This may be uncomfortable or unnerving for the patient. Accordingly, it is desirable to make to planning process as fast as possible. Since an extra non-diagnostic 3D scan is time-consuming, methods requiring a 3D scout image may be undesirable in clinical MR scanning applications.

BRIEF SUMMARY OF THE INVENTION

The present invention provides a method and system for automatic magnetic resonance (MR) brain scan planning. Embodiments of the present invention automatically plan 3D diagnostic MR brain scans using orthogonal 2D localizer images.

In one embodiment of the present invention, an MR brain scan is automatically planned based on a set of 2D orthogonal MR image slices including a transversal slice, a coronal slice, and a sagittal slice. A sagittal scanning plane is determined based on a location of the mid-sagittal plane (MSP) in the transversal and coronal slices, and a diagnostic sagittal MR scan is acquired based on the sagittal scanning plane. The corpus callosum (CC) is then segmented in a sagittal MR image slice resulting from said diagnostic sagittal MR scan. A transversal scanning plane is determined based on a location of the CC in the sagittal MR image slice and the location of the MSP in the coronal slice, and a coronal scanning plane is determined based on a location of the CC in the sagittal MR image slice and the location of the MSP in the transversal slice. Diagnostic transversal and coronal MR scans can then be acquired based on the transversal scanning plane and the coronal scanning plane, respectively.

In another embodiment of the present invention, an MR brain scan is automatically planned based on a template image having a defined scanning plane. Relevant landmarks to the defined scanning plane in the template image are identified. The template image is then registered to a target image based on only the relevant landmarks in order to define a scanning plane for the target image. The relevant landmarks can be pre-identified in the template image, or can be determined by detecting anatomic landmarks having a spatial relationship with the defined scanning plane.

These and other advantages of the invention will be apparent to those of ordinary skill in the art by reference to the following detailed description and the accompanying drawings.

DETAILED DESCRIPTION

The present invention is directed to a method for automatic magnetic resonance (MR) brain scan planning. Embodiments of the present invention are described herein to give a visual understanding of the segmentation method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. For example, according to various embodiments of the present invention, electronic data representing a target MR image, as well as electronic data representing training images for an active shape model are manipulated within a computer system.

According to an embodiment of the present invention, the MR brain scan planning method of the present invention can determine 3D scanning planes based on a set of 2D orthogonal MR image slices. The 2D orthogonal MR image slices can be localizer or scout images acquired by a less time-consuming MR sequence. The set of 2D orthogonal image slices includes a transversal MR image slice (transversal localizer image), a coronal MR image slice (coronal localizer image), and a sagittal MR images slice (sagittal localizer image).

Figure 1:
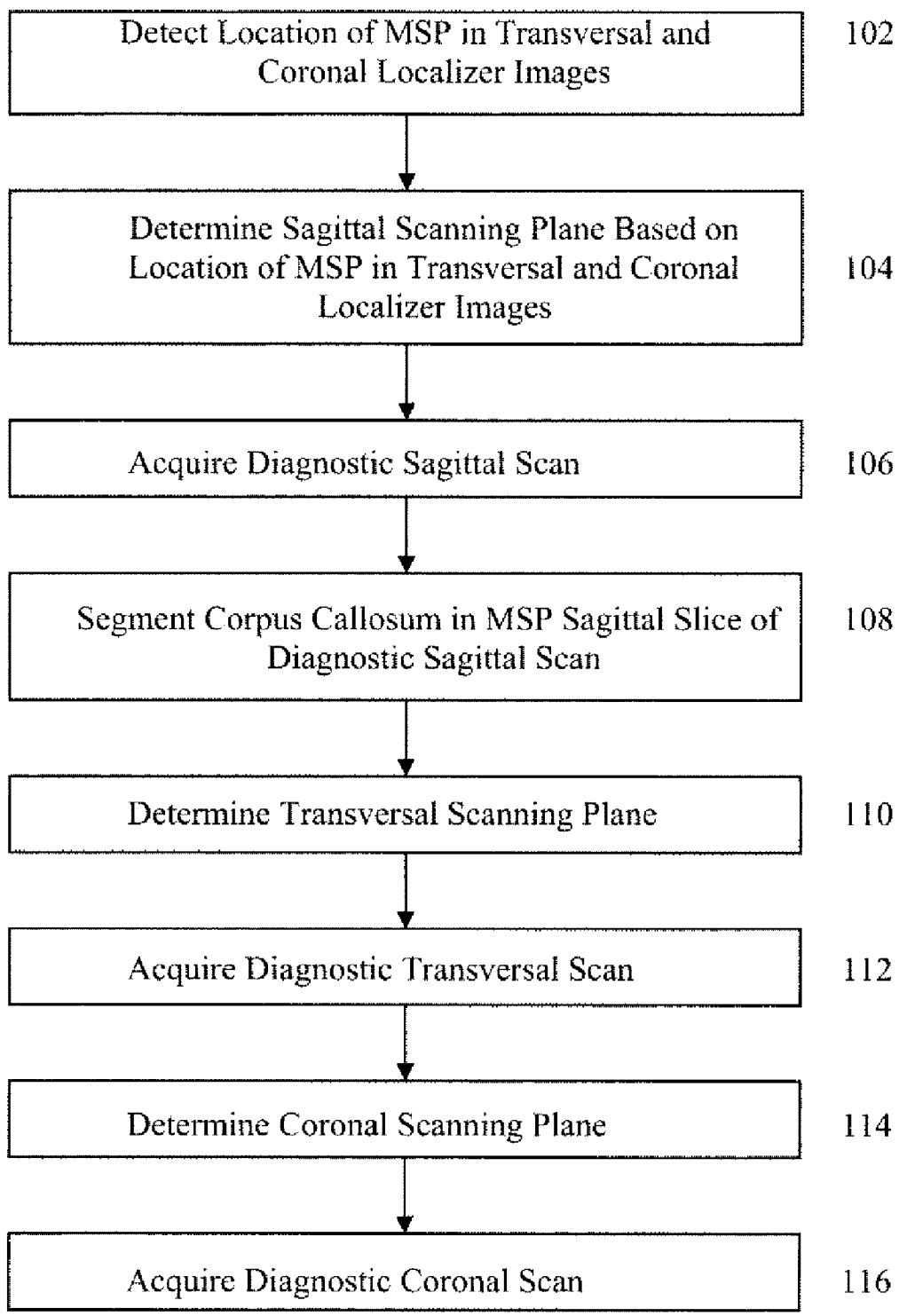
FIG. 1 illustrates an automatic magnetic resonance (MR) brain scan planning method according to an embodiment of the present invention.

FIG. 1 illustrates an automatic magnetic resonance (MR) brain scan planning method according to an embodiment of the present invention. The method of FIG. 1 determines scanning planes for sagittal, transversal, and coronal diagnostic MR brain scans based on a set of 2D orthogonal MR image slices including a transversal localize image and a coronal localizer image. This method automatically identifies anatomic landmarks in the brain using the localizer images and available diagnostic images, and defines the scanning planes based on these anatomic landmarks.

At step 102, the location of the mid-sagittal plane is detected in the transversal and coronal localizer images. The mid-sagittal plane is a plane which separates the two hemispheres of the brain. The location of the MSP can be represented as a line separating the hemispheres of the brain in each of the coronal and transversal localizer images. According to an embodiment of the present invention, the MSP location can be detected in each of the transversal and coronal localizer images by calculating symmetric lines to minimize the difference between two sides of each localizer images. The symmetric lines calculated in each localizer image are then fined tuned using a linear regression method with robust weights in order to determine a separation line which best separates the two hemispheres in each localizer image. This method of automatically detecting the MSP location in transversal and coronal images is described in greater detail below.

At step 104, a sagittal scanning plane is determined based on location of the MSP detected in the transversal and coronal localizer images. As described above, the MSP is represented by a line in each of the transversal and coronal localizer images. These lines define the plane of the MSP. The calculation of the MSP equation from the lines representing the MSP in the transversal and coronal localizer images is described in greater detail below. The sagittal scanning plane is determined to be parallel to the MSP.

At step 106, a diagnostic sagittal scan is acquired. The diagnostic sagittal scan is a high-resolution MR scan with desired contrast based on the sagittal scanning plane. The diagnostic sagittal scan in acquired by scanning parallel to the sagittal scanning plane using an MR scanning device. The diagnostic sagittal scan results in a plurality of sagittal image slices, each of which is an image of the brain in a plane parallel to the MSP. One of the sagittal image slices of the diagnostic sagittal scan is an image of the MSP. This slice is referred to herein as the "MSP" sagittal slice.

Figure 2:
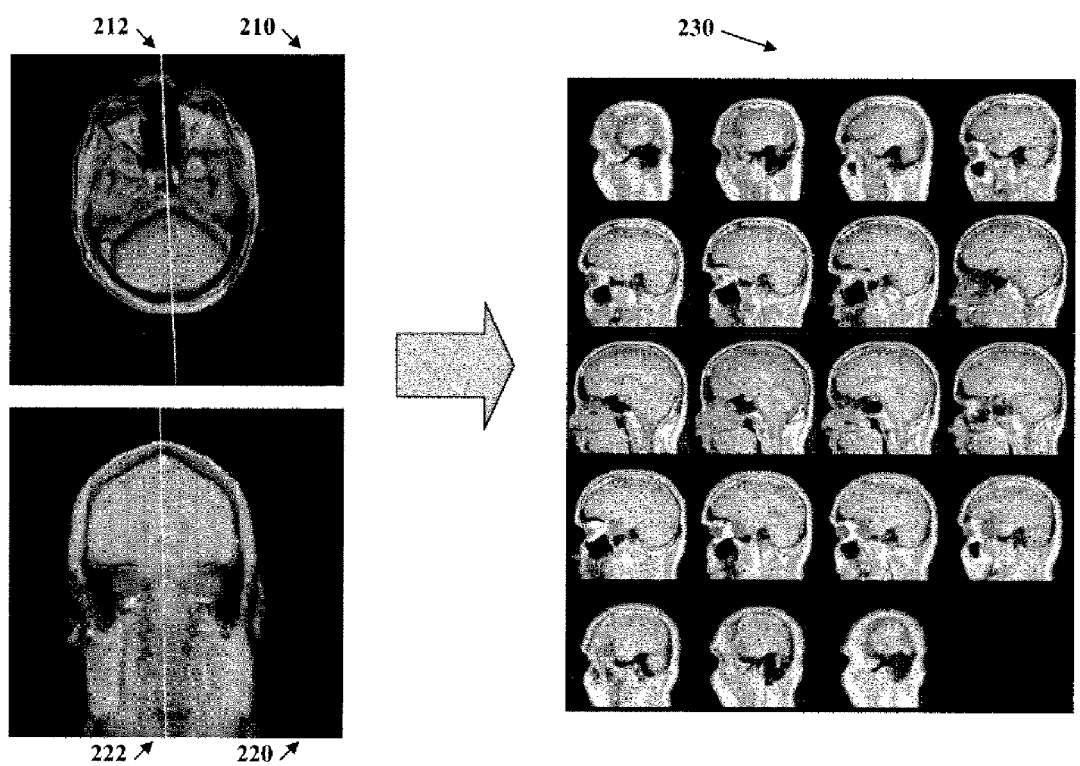
FIG. 2 illustrates exemplary transversal and coronal images used to determine a sagittal scanning plane.

FIG. 2 illustrates exemplary transversal and coronal images used to determine a sagittal scanning plane. As illustrated in FIG. 2, a transversal localizer image 210 and a coronal localizer image 220 are used to determine a sagittal scanning plane resulting in a diagnostic sagittal scan 230. Separation lines 212 and 222 representing the location of the MSP are detected in the transversal localizer image 210 and the coronal localizer image 220, respectively. The separation lines 212 and 222 define the plane of the MSP, which is used as the sagittal scanning plane. Accordingly, the diagnostic sagittal scan 230 based on the sagittal scanning plane results in a plurality of sagittal image slices parallel to the MSP. The coronal image slice used in this step can be a coronal localizer image. However, it is also possible to use a coronal image slice of the diagnostic coronal scan after the diagnostic coronal scan is acquired using step 114 and 116.

Returning to FIG. 1, at step 108, the corpus callosum (CC) is segmented in the MSP sagittal slice of the diagnostic sagittal scan. According to an embodiment of the present invention, the CC can be segmented from the MSP sagittal slice using an active shape model (ASM) with confidence weighting and region based refinement. A method for CC segmentation using an ASM with confidence weighting and region based refinement is described in detail in U.S. patent application Ser. No. 11/782,828, which is incorporated herein by reference.

At step 110, the transversal scanning plane is determined. The transversal scanning plane is determined based on the location of the MSP in the coronal localizer image and the CC segmented in the MSP sagittal image. In particular, a line connecting the bottom portions of the CC in the MSP sagittal image is combined with a line perpendicular to the MSP line in the coronal localizer image to define the transversal scanning plane. The calculation of transverse scanning plane from these two lines is similar to the calculation of MSP from the separation lines in coronal and transverse images in step 104.

At step 112, a diagnostic transversal scan is acquired. The diagnostic transversal scan is a high-resolution MR scan with good contrast for anatomic structures of interest based on the transversal scanning plane. The diagnostic transversal scan is acquired by scanning parallel to the transversal scanning plane using an MR scanning device. The diagnostic transversal scan results in a plurality of transversal image slices, each of which is an image of the brain in a plane parallel to the transversal scanning plane.

Figure 3:
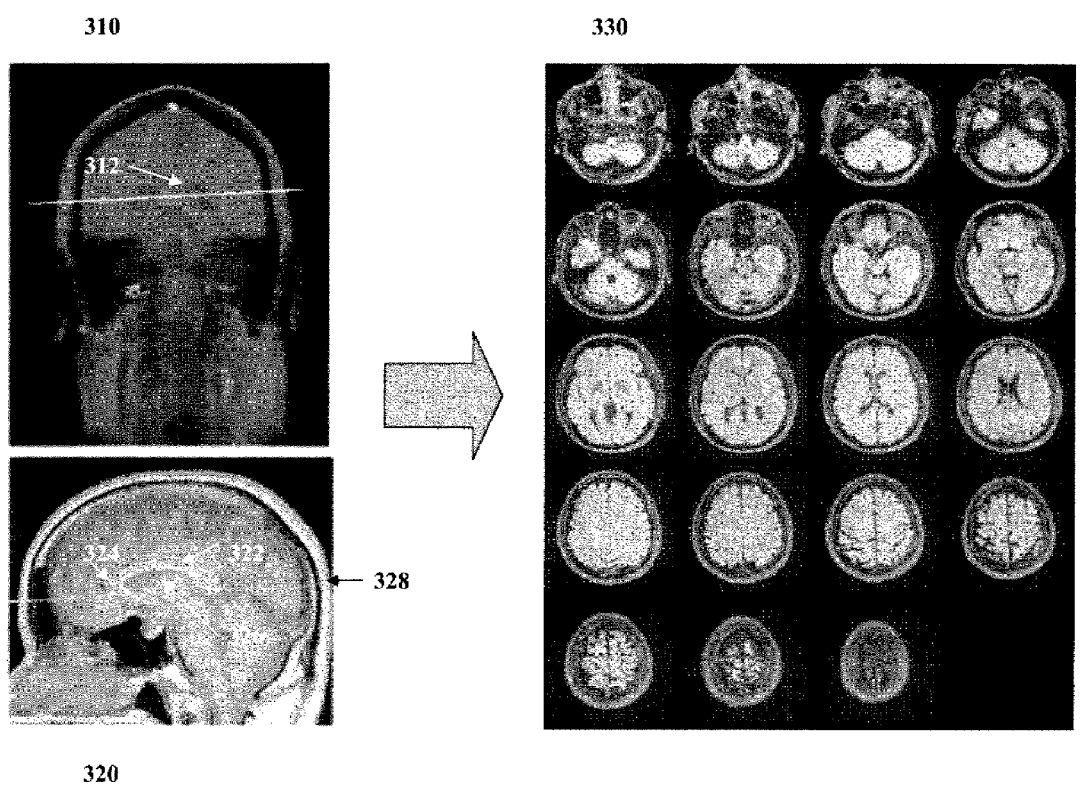
FIG. 3 illustrates exemplary coronal and sagittal images used to determine a transversal scanning plane.

FIG. 3 illustrates exemplary coronal and sagittal images used to determine a transversal scanning plane. As illustrated in FIG. 3, a coronal localizer image 310 and an MSP sagittal image 320 are used to determine a transversal scanning plane resulting in a diagnostic transversal scan 330. A line 312 is detected which is perpendicular to the line representing the location of the MSP in the coronal localizer image 310. A CC boundary 322 separating the CC 324 and the ventricle 326 is detected in the MSP sagittal image 320 in the CC segmentation of step 108. A line 328 connecting the bottom portions of the CC 324 is detected based on the segmented CC boundary 322. The lines 312 and 328 define the transversal scanning plane. Accordingly, the diagnostic transversal scan 330 based on the transversal scanning plane results in a plurality of transversal image slices parallel to the transversal scanning plane.

Returning to FIG. 1, at step 114, the coronal scanning plane is determined. The coronal scanning plane is determined based on the location of the MSP in a transversal image slice and the CC segmented in the MSP sagittal image. In particular, a line perpendicular to the MSP line in the transversal image slice is combined with a line perpendicular to the tope surface of the ventricle in the MSP sagittal image to define the coronal scanning plane. The calculation of coronal scanning plane from these two lines is similar to the calculation of MSP from the separation lines in coronal and transverse images in step 104. The transversal image slice used in this step can be a transversal image slice of the diagnostic transversal scan.

However, it is also possible to use the transversal localizer image so that this step can be performed prior to or in parallel with step 110.

At step, 116 a diagnostic coronal scan is acquired. The diagnostic coronal scan is a high-resolution MR scan based on the coronal scanning plane. The diagnostic coronal scan in acquired by scanning parallel to the coronal scanning plane using an MR scanning device. The diagnostic coronal scan results in a plurality of transversal image slices, each of which is an image of the brain in a plane parallel to the coronal scanning plane.

Figure 4:
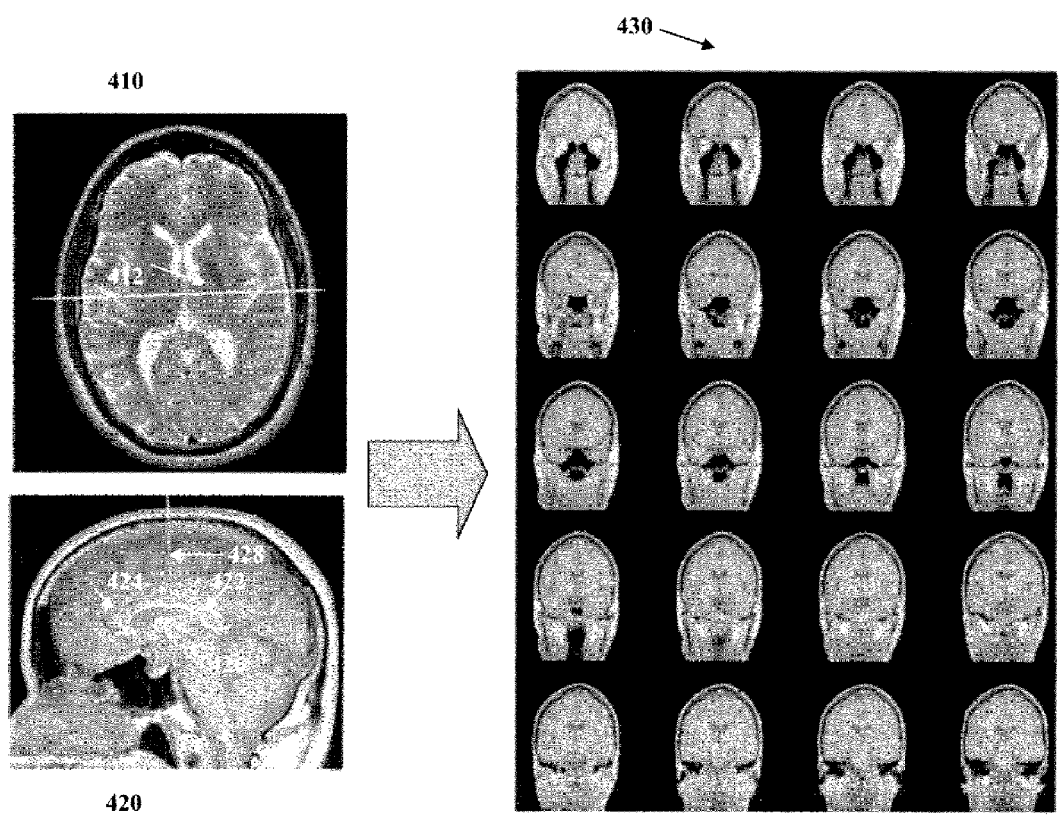
FIG. 4 illustrates exemplary transversal and sagittal images used to determine a coronal scanning plane.

FIG. 4 illustrates exemplary transversal and sagittal images used to determine a coronal scanning plane. As illustrated in FIG. 4, a transversal image slice 410 of the diagnostic transversal scan and an MSP sagittal image 420 are used to determine a coronal scanning plane resulting in a diagnostic coronal scan 430. A line 412 is detected which is perpendicular to the line representing the location of the MSP in the transversal image slice 410. A CC boundary 422 separating the CC 424 and the ventricle 426 is detected in the MSP sagittal image 420 in the CC segmentation of step 108. A line 428 is detected which is perpendicular to the top surface of the ventricle 426 based on the segmented CC boundary 422. The lines 412 and 428 define the coronal scanning plane. Accordingly, the diagnostic coronal scan 430 based on the coronal scanning plane results in a plurality of coronal image slices parallel to the coronal scanning plane.

Although the method of FIG. 1 determines the transversal scanning plane (step 110) prior to determining the coronal scanning plane (step 114), the present invention is not limited thereto. These steps can be performed in any order or in parallel When one of the transversal or coronal scanning planes is determined prior to the other, a slice in the resulting diagnostic scan from the prior determined scanning plane can be used in determining the other scanning plane. However, it is also possible that the localizer images are used for determining both scanning planes when the scanning planes are determined in parallel.

Figure 5:
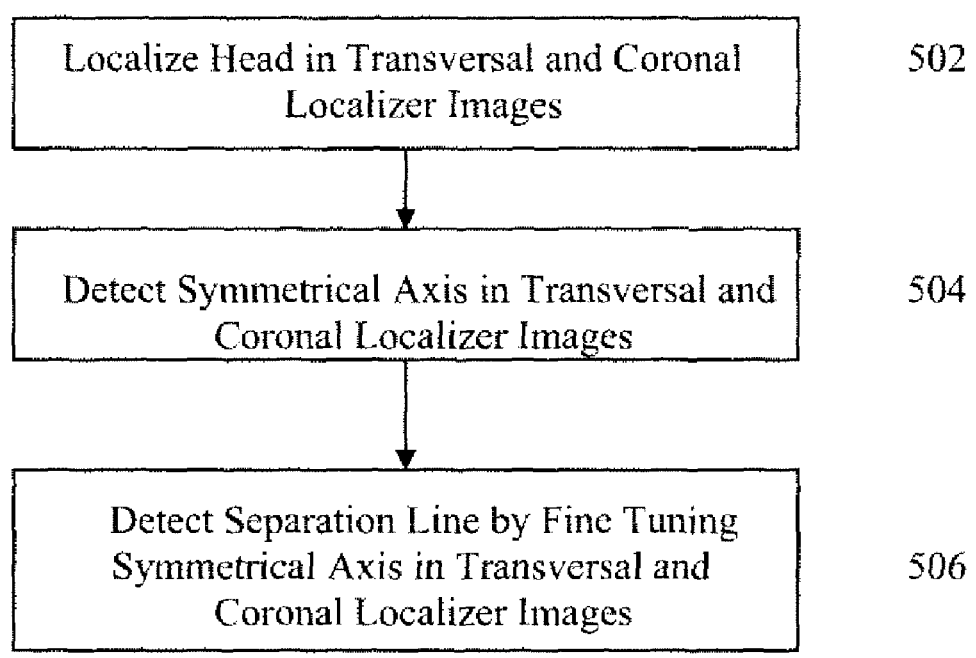
FIG. 5 illustrates a method for detecting a location of the mid-sagittal plane (MSP) in transversal and coronal localizer images according to an embodiment of the present invention.

FIG. 5 illustrates a method for detecting a location of the mid-sagittal plane (MSP) in transversal and coronal localizer images according to an embodiment of the present invention. Accordingly, step 102 of FIG. 1 is explained in greater detail by referring to FIG. 5.

Figure 6:
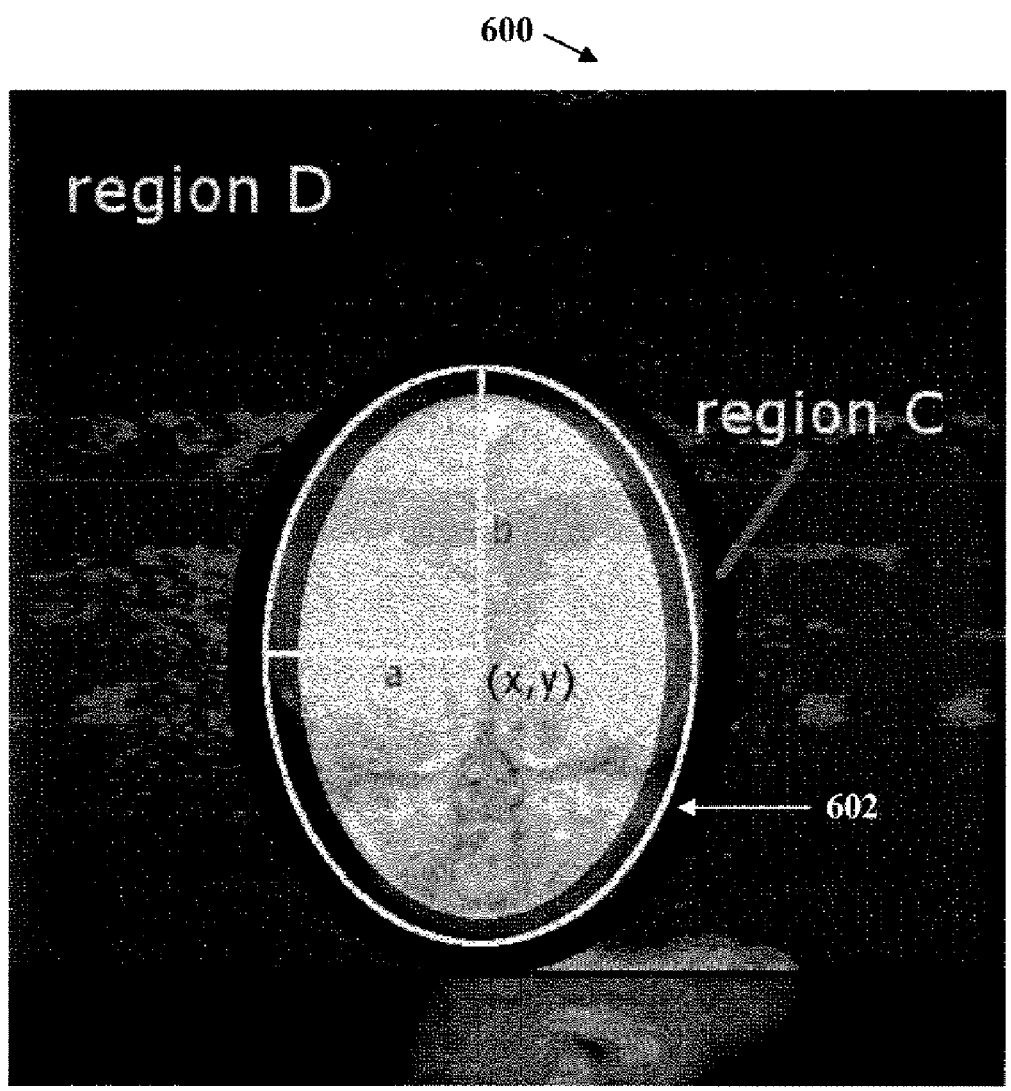
FIG. 6 illustrates head localization in an exemplary coronal localizer image.

As illustrated in FIG. 5, at step 502, the head is localized in the transversal and coronal localizer images. FIG. 6 illustrates head localization in an exemplary coronal localizer image 600. The localization is performed similarly in a transversal localizer image. Step 502 is described while referring to FIGS. 5 and 6. The head is localized in the coronal and transversal localizer images by fitting an ellipse 602 to the image to maximize the measurement of fitting, i.e., $$\{cx, cy, a, b\} = \arg\max_{\{cx,cy,a,b\}} \int_{(x,y) \in C} |\nabla I(x, y)| dx dy \cdot P(cx, cy, a, b), \quad (1)$$

where I represents the image data with I(x,y) referring to the pixel value at location (x,y). (cx,cy) is the center of the ellipse 602, a and b are the lengths of the long axis and the short axis of the ellipse 602, respectively. P(cx,cy,a,b) models prior probability of the parameters and $$\int_{(x,y) \in C} |\nabla I(x, y)| dx dy$$

measures the strength of the image gradient in a boundary region C of the ellipse 602. As illustrated in FIG. 6, the boundary region C is a narrow band with a certain width around the outline of the ellipse 602, where outline of the ellipse 602 represents the set of the points satisfying equation $$\left(\frac{x-cx}{a}\right)^2 + \left(\frac{y-cy}{b}\right)^2 = 1.$$

With an assumption of independence, P(cx,cy,a,b)=P(cx)P(cy)P(a)P(b), where P(cx)=1, P(cy)=1, $$P(a) = \frac{1}{\sqrt{2\pi} \, w/4} e^{\frac{-(a-w/4)^2}{2(w/4)^2}} \text{ and } P(b) = \frac{1}{\sqrt{2\pi} \, h/4} e^{\frac{-(b-h/4)^2}{2(h/4)^2}},$$

where w is the width of the image, and h is the height of the image. The roll and pitch of head does not need to be modeled since head posture is typically immobilized during the MR scanning process and head localization only needs to give an approximate estimation of the head position for next step calculation, and the model in Equation (1) is sufficient for this purpose.

At step 504, a symmetrical axis is detected in each of the transversal and coronal localizer images. The symmetrical axis is defined as L, where $$L = \arg\min_{L} \int_{(x,y) \in D} (I(x, y) - I(x', y'))^2 dx dy, \quad (2)$$

where (x',y') is the symmetric point of (x,y) with respect to line L, and region D (see FIG. 6) is defined as a rectangular area that covers from the top the image to the bottom of the ellipse 602 defined in step 502. Region D excludes irrelevant anatomy in the image, such as the shoulders in FIG. 6. Both equations (1) and (2) can be optimized using the Simplex method, such as the method described in W. H. Press et al., "Numerical Recipes in C", Cambridge University Press, Second Edition, 1992.

Figure 7:
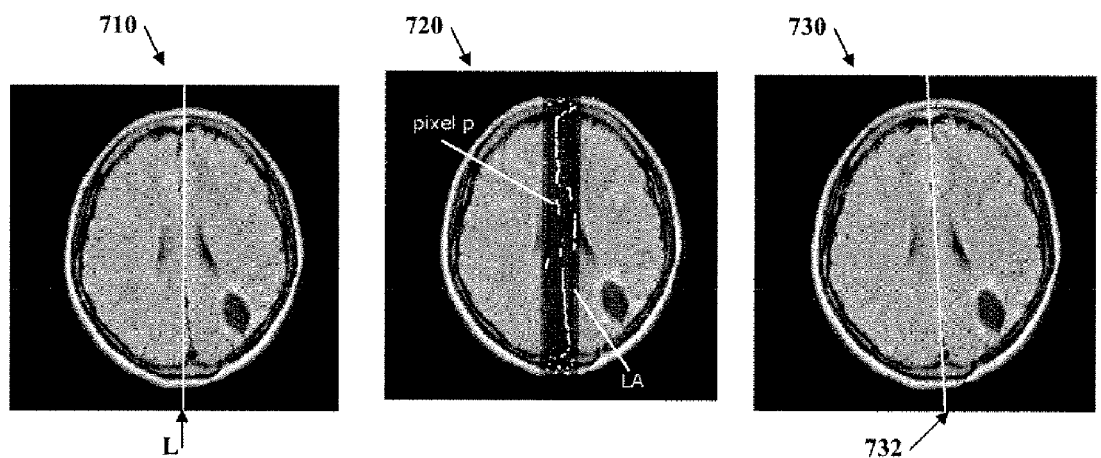
FIG. 7 illustrates detection of a separation line in an exemplary transversal localizer image.

At step 506, a separation line is detected by fine tuning the symmetrical axis in each of the transversal and coronal localizer images. FIG. 7 illustrates detection of the separation line in an exemplary transversal localizer image. It is to be understood that this can be similarly performed in a coronal localizer image. Image 710 illustrates the symmetrical line L detected for the transversal localizer image. As illustrated in image 720, an area adjacent to the symmetrical line L can be denoted as LA. The left and right sides of LA are both 0.1a away from the symmetrical line L, where a is the short axis of the ellipse in equation (1). In order to fine tune the symmetrical axis L, pixels located between the hemispheres of the brain are detected. Each such pixel is denoted as a point p, and the set of the pixels p detected between the hemispheres of the brain can be denoted as M. The pixel intensities of every horizontal line in the area LA are correlated with a symmetric array [1,1,0,1,1]. Due to the symmetry of brain structure across the MSP, in each horizontal line in LA a point p is detected as the point that has the largest absolute value. A linear regression with robust weights can than be used to determine a separation line separating the hemispheres based on the points p in the detected set M. Image 730 illustrates the separation line 732 detected for the transversal localizer image. The separation lines detected in each of the transversal and coronal localizer images represent the location of the MSP in the transversal and coronal localizer images.

Figure 8:
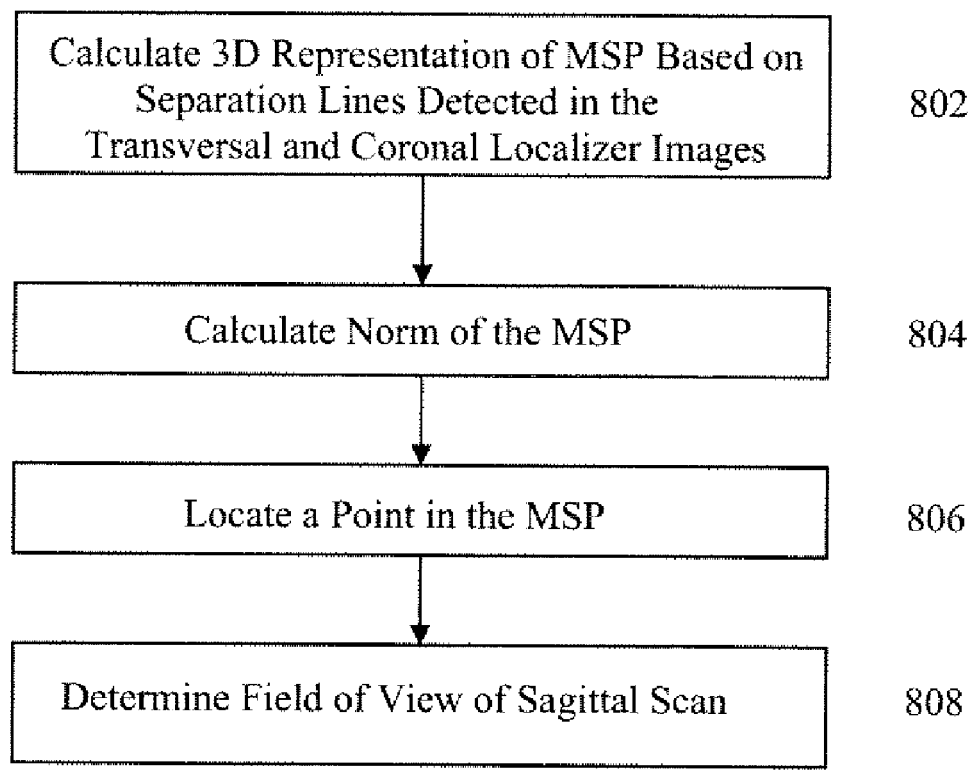
FIG. 8 illustrates a method for determining the sagittal scanning plane based on the detected location of the MSP in the transversal and coronal localizer images according to an embodiment of the present invention.

FIG. 8 illustrates a method for determining the sagittal scanning plane based on the detected location of the MSP in the transversal and coronal localizer images according to an embodiment of the present invention Accordingly, step 104 of FIG. 1 is explained in greater detail by referring to FIG. 8.

At step 802, a 3D representation of the MSP is calculated based on the separation lines detected in the transversal and coronal localizer images. The 3D representation of the MSP is calculated based upon the 2D geometry of the separation lines representing the location of the MSP in each of the transversal and coronal localizer images, as well as 3D information associated with each of the coronal and transversal localizer images. The 3D information corresponds to the physical coordinate of pixels in each of the localizer images. For each of the transversal and coronal localizer images, let the coordinate vector of the left and upper corner of the slice be $\vec{pos}$, let the row vector of the slice, which is the unit vector pointing along the height of the slice, be $\vec{row}$, and let the column vector of the slice, which is the unit vector pointing along the width of the slice, be $\vec{col}$. The separation line in the 2D space of the slice can be represented as $x=ky+c$. The 3D parametric representation of the line is $\vec{p}=\vec{p}_0+t\cdot\vec{v}$, where $\vec{p}_0=\vec{pos}+c\cdot\vec{col}$, and $\vec{v}$ is represented as $\alpha\cdot\vec{col}+\beta\cdot\vec{row}$, so that $\alpha/\beta=k$ and $\alpha^2+\beta^2=1$. Values of $\vec{pos}$, $\vec{col}$ and $\vec{row}$ can be retrieved from the DICOM header associated with the image slice.

At step 804, the norm of the MSP is calculated. The direction in 3D of the separation lines in coronal and transverse localizer images can be denoted as $\vec{a}$ and $\vec{b}$, respectively. The norm of the MSP can be calculated as $\vec{n}=\vec{a}\times\vec{b}$.

At step 806, a point in the MSP is located. Let $p_1$ and $p_2$ be the closest points to each other in the two separation lines. The MSP should pass through the mid-point of $p_1$ and $p_2$. To determine the coordinates of $p_1$ and $p_2$, according to the 3D representation of the lines, let $\vec{p}_1=\vec{s}_1+t_1\cdot\vec{v}_1$ and $\vec{p}_2=\vec{s}_2+t_2\cdot\vec{v}_2$. The distance between $p_1$ and $p_2$ is calculated as $L=\|\vec{p}_1-\vec{p}_2\|^2$. The equation array $$\frac{\partial L}{\partial t_1}=0 \text{ and } \frac{\partial L}{\partial t_2}=0$$

can be solved to obtain the value of $t_1$ and $t_2$. Let the mid-point of $\vec{p}_1$ and $\vec{p}_2$ be $\vec{p}_m$. The MSP is then represented as $(\vec{q}-\vec{p}_m)\cdot\vec{n}=0$, where $\vec{q}$ is variable representing a 3D point in the MSP. The MSP represents the sagittal scanning plane which determines the orientation of an MR scanner for performing a diagnostic sagittal scan.

Figure 9:
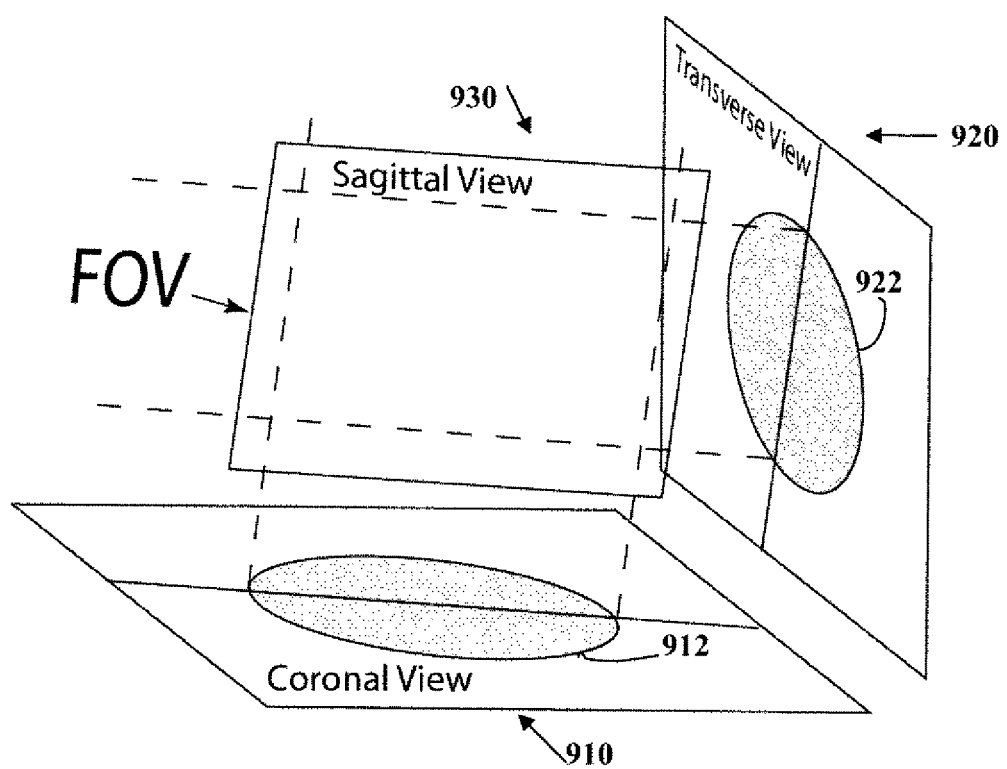
FIG. 9 illustrates determination of a field of view of the sagittal scanning plane.

At step 808, a field of view (FOV) of the sagittal scan is determined. Although the orientation of the scanner for a diagnostic sagittal scan is determined so that the scan is parallel to the sagittal scanning plane (MSP), the FOV of the sagittal scan refers to the height and width of each slice in the diagnostic sagittal scan. The FOV of the sagittal scan is determined based on the ellipses fit to the head in the coronal and transversal localizer images in step 702. FIG. 9 illustrates determination of a field of view of the sagittal scanning plane. As illustrated in FIG. 9, the long axis of ellipse 912 in the coronal localizer image 910 determines the height of the head in the sagittal view 930. The long axis of the ellipse 922 in the transversal localizer image 920 determines the width of the head in the sagittal view 930. The FOV is a rectangle that is slightly larger than the inferred head size in the sagittal view 930.

Figure 10:
FIG. 10 illustrates an exemplary MSP sagittal slice constructed based on the detected location of the MSP in transversal and coronal localizer images.

FIG. 10 illustrates an exemplary MSP sagittal slice constructed using the methods of FIGS. 5 and 8 based on the location of the MSP in transversal and coronal localizer images. Image 1010 is a coronal localizer image and image 1020 is a transversal localizer image. Separation lines 1012 and 1022 representing the location of the MSP are detected in the coronal and transversal localizer images 1010 and 1020, respectively Image 1030 is a sagittal view of the MSP calculated based on the separation lines 1012 and 1022 detected in the coronal and transversal localizer images 1010 and 1020, respectively. A subsequent diagnostic sagittal scan is performed along planes parallel to the MSP view 1030. The dotted lines in images 1010 and 1020 which are parallel to the detected MSP represent the scan FOV which is calculated based on the ellipses fit in the head localization step (step 702).

Figure 11:
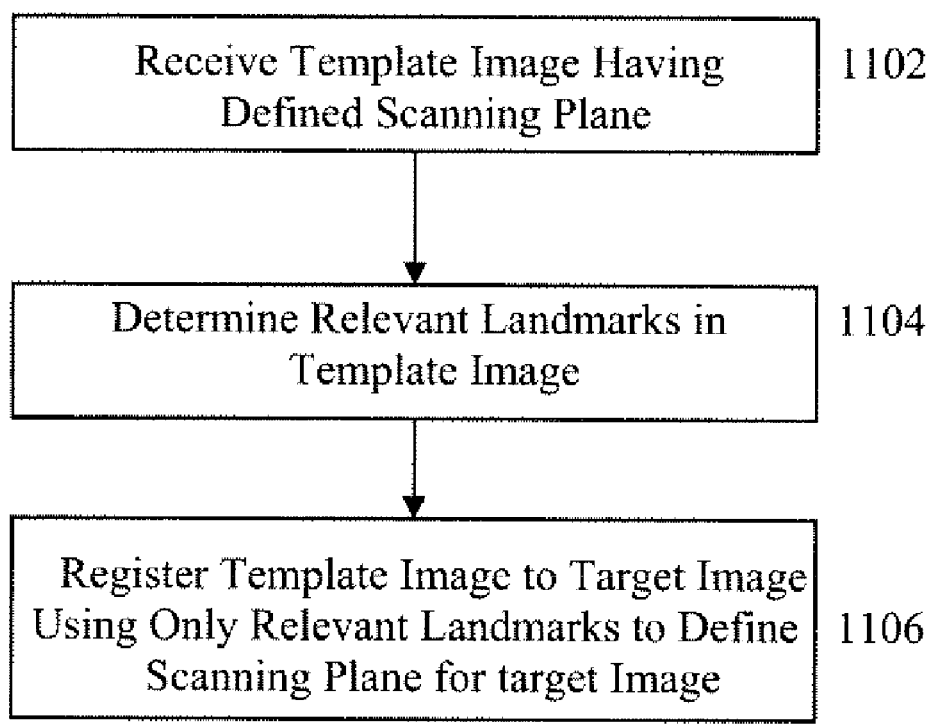
FIG. 11 illustrates an MR brain scan planning method according to another embodiment of the present invention.

FIG. 11 illustrates an MR brain scan planning method according to another embodiment of the present invention. The method of this embodiment maps a pre-defined scanning plane to a current scan using image registration methods. This method provides users a flexible option to create a custom scanning plane, which can be used consistently. At step 1102, a template image having a defined scanning plane is received. The scanning plane can be manually defined by a user on the template image. It is possible that a computer system performing the steps of this method receive the template by receiving a user input to define the scanning plane on an image stored by the computer system. It is also possible that the computer system receives or loads a previously stored template image having the scanning plane defined thereon.

Figure 12:
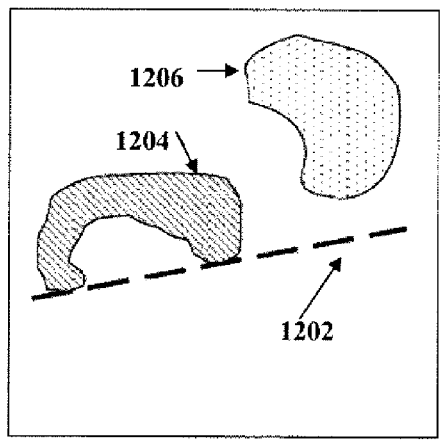
FIG. 12 illustrates exemplary relevant landmarks for a defined scanning plane.
Figure 12:
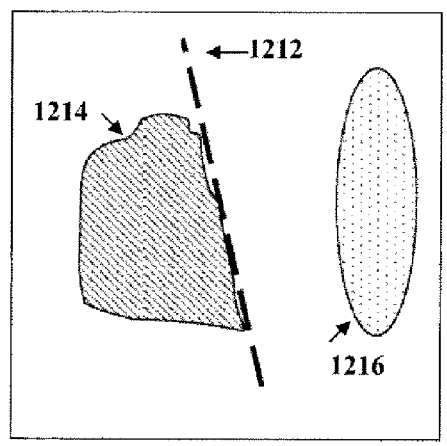

At step 1104, relevant landmarks are determined in the template image. As used herein, the term "relevant landmarks" refers to landmarks in an image which are close to the scanning plane and thus influence the mapping of the geometry of the defined scanning plane by registration. The relevant landmarks can be identified by a user on the template image. Such relevant landmarks can be landmarks used by the user to align the scanning plane. FIG. 12 illustrates exemplary relevant landmarks for a defined scanning plane. As illustrated in example A of FIG. 12, for the manually defined scanning plane 1202, landmark 1204 is a relevant landmark and landmark 1206 is an irrelevant landmark. As illustrated in example B of FIG. 12, for the manually defined scanning plane 1212, landmark 1214 is a relevant landmark and landmark 1216 is an irrelevant landmark.

Figure 13:
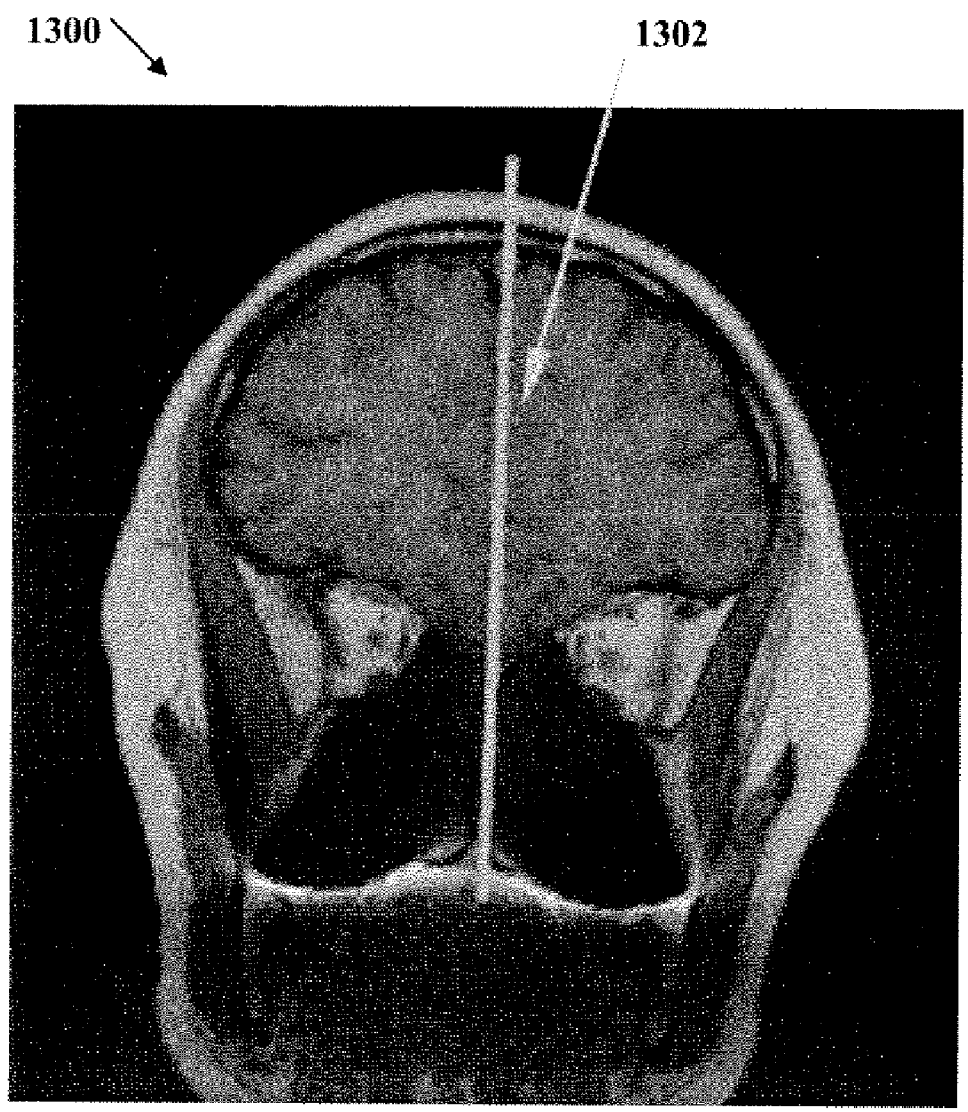
FIG. 13 illustrates an exemplary scanning plane for which the MSP is a relevant landmark.

According to an alternate implementation, the relevant landmarks can be automatically identified based using a computer-based method that checks a spatial relationship between the defined scanning plane and anatomic landmarks in the template image. FIG. 13 illustrates an exemplary scanning plane for which the MSP is a relevant landmark. As illustrated in FIG. 13, template image 1300 is coronal MR image slice having a manually defined scanning plane 1302. The manually defined scanning plane 1302 for the template image 1300 correlates well with the MSP, thus a computer-based method for automatically identifying relevant landmarks can determine that the MSP is the relevant landmark for registration.

Returning to FIG. 11, at step 1106, the template image is registered to a target image using only relevant landmarks to define the scanning plane for the target image. The target image can be a localizer image used for scan planning. The template image is registered to the target image using only the relevant landmarks to the defined scanning plane, while ignoring all irrelevant landmarks in the template image. Accordingly, the scanning plane is mapped to the target image, and the size, position, and orientation of the scanning plane is adjusted only based on the relevant landmarks.

Traditional landmark based registration techniques map template images to target images using all available landmarks within the entire image domain. Since the method of FIG. 11 utilizes only landmarks relevant to the defined scanning plane for template registration, this method can more accurately and consistently map the defined scanning plane to target images to define scanning planes of subsequent scans.

Figure 14:
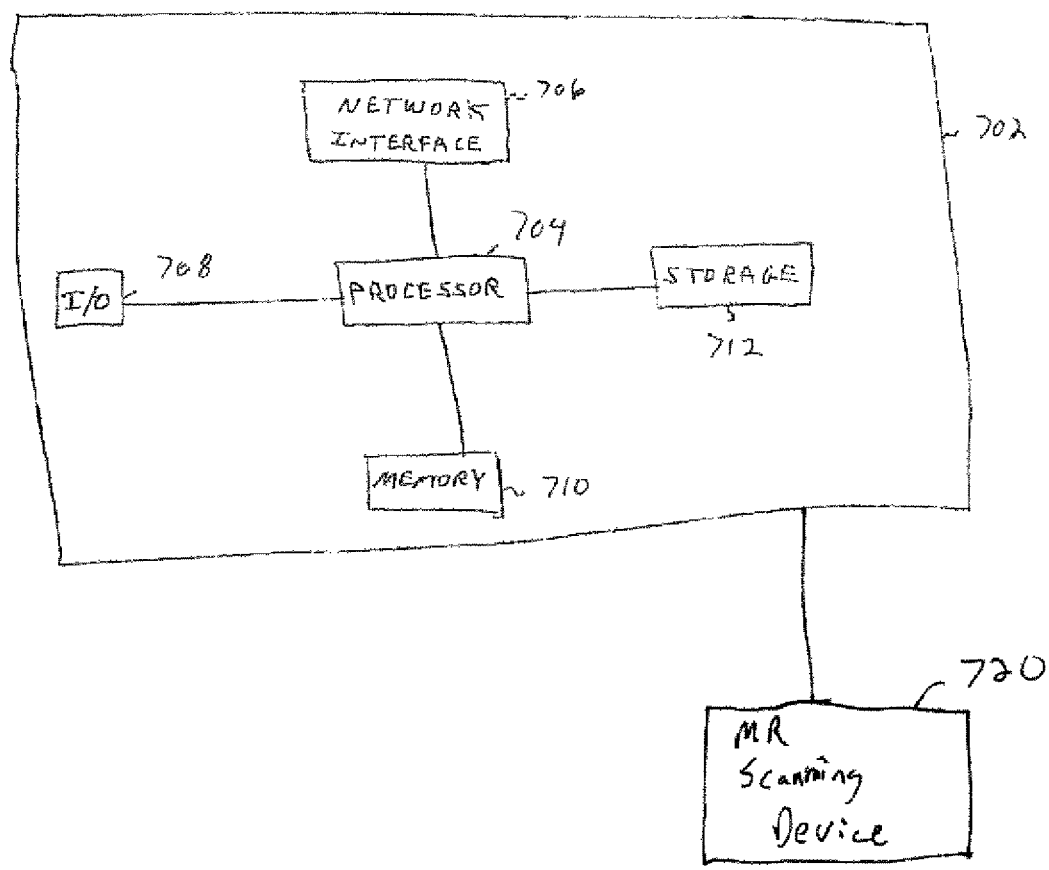
FIG. 14 is a high level block diagram of a computer capable of implementing the present invention.

The above-described methods for MR brain scan planning can be implemented on a computer using well-known computer processors, memory units, storage devices, computer software, and other components. A high level block diagram of such a computer is illustrated in FIG. 14. Computer 1402 contains a processor 1404 which controls the overall operation of the computer 1402 by executing computer program instructions which define such operation. The computer program instructions may be stored in a storage device 1412 (e.g., magnetic disk) and loaded into memory 1410 when execution of the computer program instructions is desired. Thus, applications for performing the above described method steps can be defined by the computer program instructions stored in the memory 1410 and/or storage 1412 and controlled by the processor 1404 executing the computer program instructions. Furthermore, image data corresponding to MR brain images, including low-resolution localizer images and high-resolution diagnostic images can be stored in the memory 1410 and/or the storage 1412. An MR scanning device 1420 which generate MR images can be connected to the computer 1402 to input MR images to the computer 1402. It is possible to implement the MR scanning device and the computer 1402 as one device. It is also possible the MR scanning device 1420 and the computer 1402 communicate wirelessly through a network. The computer 1402 also includes one or more network interfaces 1406 for communicating with other devices via a network. The computer 1402 also includes other input/output devices 1408 that enable user interaction with the computer 1402 (e.g., display, keyboard, mouse, speakers, buttons, etc.) One skilled in the art will recognize that an implementation of an actual computer could contain other components as well, and that FIG. 14 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention Those skilled in the art could implement various other feature combinations without departing from the scope and spirit of the invention.

What is claimed is:

1. A method for automatic magnetic resonance (MR) brain scan planning based on a set of 2D orthogonal MR image slices including a transversal slice, a coronal slice, and a sagittal slice, comprising:
   determining a sagittal scanning plane based on a location of a mid-sagittal plane (MSP) in each of the transversal slice and the coronal slice;
   acquiring a diagnostic sagittal MR scan based on said sagittal scanning plane;
   segmenting a corpus callosum (CC) in a sagittal MR image slice resulting from said diagnostic sagittal MR scan;
   determining a transversal scanning plane based on a location of the CC in the sagittal MR image slice and the location of the MSP in the coronal slice; and
   determining a coronal scanning plane based on the location of the CC in the sagittal MR image slice and the location of the MSP in the transversal slice.

2. The method of claim 1, further comprising:
   detecting the location of the MSP in each of the transversal slice and the coronal slice.

3. The method of claim 2, wherein said step of detecting the location of the MSP in each of the transversal slice and the coronal slice comprises:
   localizing a shape of a head in each of the transversal slice and the coronal slice;
   detecting a symmetric axis in each of the transversal slice and the coronal slice; and
   detecting a separation line representing the location of the MSP by fine tuning the symmetric axis using linear regression with robust weights in each of the transversal slice and the coronal slice.

4. The method of claim 3, wherein said step of detecting a separation line representing the location of the MSP comprises:
   detecting pixels within an area adjacent to the symmetric axis that are between brain hemispheres; and
   performing linear regression with robust weights on pixels detected between the brain hemispheres.

5. The method of claim 4, wherein said step of detecting pixels comprises:
   correlating pixel intensity of the pixels within said area along each of a plurality of horizontal lines with a symmetric array [1 1 0 1 1]; and
   detecting a pixel having a correlated pixel intensity with the largest absolute value in each of the plurality of horizontal lines.

6. The method of claim 3, wherein said step of determining a sagittal scanning plane comprises:
   calculating a 3D representation of the MSP based on the separation lines detected in the transversal and coronal slices;
   calculating a norm of the MSP;
   locating a point on the MSP based on the 3D representation of the MSP, wherein said point on the MSP and said norm of the MSP define the sagittal scanning plane; and
   determining a sagittal scanning field of view based on the shape of the head localized in each of the transversal slice and the coronal slice.

7. The method of claim 6, wherein said step of determining a sagittal scanning field of view comprises:
   determining a height of the sagittal scanning field of view based on the shape of the head localized in the coronal slice; and
   determining a width of the sagittal scanning field of view based on the shape of the head localized in the transversal slice.

8. The method of claim 1, wherein said step of segmenting a corpus callosum (CC) comprises:
  segmenting the CC using an active shape model with confidence weighting and region-based refinement.

9. The method of claim 1, further comprising:
  acquiring a diagnostic transversal MR scan based on said transversal scanning plane; and
  acquiring a diagnostic coronal MR scan based on said coronal scanning plane.

10. The method of claim 1, wherein said transversal slice comprises a transversal localizer image and said coronal slice comprise a coronal localizer image.

11. An apparatus for automatic magnetic resonance (MR) brain scan planning based on a set of 2D orthogonal MR image slices including a transversal slice, a coronal slice, and a sagittal slice, comprising:
  means for determining a sagittal scanning plane based on a location of a mid-sagittal plane (MSP) in each of the transversal slice and the coronal slice;
  means for acquiring a diagnostic sagittal MR scan based on said sagittal scanning plane;
  means for segmenting a corpus callosum (CC) in a sagittal MR image slice resulting from said diagnostic sagittal MR scan;
  means for determining a transversal scanning plane based on a location of the CC in the sagittal MR image slice and the location of the MSP in the coronal slice; and
  means for determining a coronal scanning plane based on the location of the CC in the sagittal MR image slice and the location of the MSP in the transversal slice.

12. The apparatus of claim 11, further comprising;
  means for detecting the location of the MSP in each of the transversal slice and the coronal slice.

13. The apparatus of claim 12, wherein said means for detecting the location of the MSP in each of the transversal slice and the coronal slice comprises:
  means for localizing a shape of a head in each of the transversal slice and the coronal slice;
  means for detecting a symmetric axis in each of the transversal slice and the coronal slice; and
  detecting a separation line representing the location of the MSP by fine tuning the symmetric axis using linear regression with robust weights in each of the transversal slice and the coronal slice.

14. The apparatus of claim 13, wherein said means for determining a sagittal scanning plane comprises:
  means for calculating a 3D representation of the MSP based on the separation lines detected in the transversal and coronal slices;
  means for calculating a norm of the MSP;
  means for locating a point on the MSP based on the 3D representation of the MSP, wherein said point on the MSP and said norm of the MSP define the sagittal scanning plane; and
  means for determining a sagittal scanning field of view based on the shape of the head localized in each of the transversal slice and the coronal slice.

15. The apparatus of claim 11, wherein said means for segmenting a corpus callosum (CC) comprises:
  means for segmenting the CC using an active shape model with confidence weighting and region-based refinement.

16. A non-transitory computer readable medium encoded with computer executable instructions for performing a method for automatic magnetic resonance (MR) brain scan planning based on a set of 2D orthogonal MR image slices including a transversal slice, a coronal slice, and a sagittal slice, the computer executable instructions defining steps comprising:
  determining a sagittal scanning plane based on a location of a mid-sagittal plane (MSP) in each of the transversal slice and the coronal slice;
  acquiring a diagnostic sagittal MR scan based on said sagittal scanning plane;
  segmenting a corpus callosum (CC) in a sagittal MR image slice resulting from said diagnostic sagittal MR scan;
  determining a transversal scanning plane based on a location of the CC in the sagittal MR image slice and the location of the MSP in the coronal slice; and
  determining a coronal scanning plane based on the location of the CC in the sagittal MR image slice and the location of the MSP in the transversal slice.

17. The non-transitory computer readable medium of claim 16, further comprising computer executable instructions defining the step of:
  detecting the location of the MSP in each of the transversal slice and the coronal slice.

18. The non-transitory computer readable medium of claim 17, wherein the computer executable instructions defining the step of detecting the location of the MSP in each of the transversal slice and the coronal slice comprise computer executable instructions defining the steps of:
  localizing a shape of a head in each of the transversal slice and the coronal slice;
  detecting a symmetric axis in each of the transversal slice and the coronal slice; and
  detecting a separation line representing the location of the MSP by fine tuning the symmetric axis using linear regression with robust weights in each of the transversal slice and the coronal slice.

19. The non-transitory computer readable medium of claim 18, wherein the computer executable instructions defining the step of determining a sagittal scanning plane comprise computer executable instructions defining the steps of:
  calculating a 3D representation of the MSP based on the separation lines detected in the transversal and coronal slices;
  calculating a norm of the MSP;
  locating a point on the MSP based on the 3D representation of the MSP, wherein said point on the MSP and said norm of the MSP define the sagittal scanning plane; and
  determining a sagittal scanning field of view based on the shape of the head localized in each of the transversal slice and the coronal slice.

\* \* \* \* \*